(12) United States Patent
Johansen

(10) Patent No.: US 7,432,352 B2
(45) Date of Patent: Oct. 7, 2008

(54) HYBRID MOLECULES HAVING FACTOR VII/VIIA ACTIVITY

(75) Inventor: Nils Langeland Johansen, Coppenhagen (DK)

(73) Assignee: Novo Nordisk Healthcare AG, Zurich (CH)

(*) Notice: Subject to any disclaimer, the term of this patent is extended or adjusted under 35 U.S.C. 154(b) by 73 days.

(21) Appl. No.: 11/393,327

(22) Filed: Mar. 30, 2006

(65) Prior Publication Data

US 2006/0258851 A1 Nov. 16, 2006

Related U.S. Application Data

(63) Continuation of application No. PCT/DK2004/000678, filed on Oct. 7, 2004.

(60) Provisional application No. 60/509,849, filed on Oct. 9, 2003.

(30) Foreign Application Priority Data

Oct. 7, 2003 (DK) .............................. 2003 01472

(51) Int. Cl.
*C07K 1/00* (2006.01)

(52) U.S. Cl. ................... 530/350; 530/300; 435/7.1; 435/69.6; 435/13

(58) Field of Classification Search ........ None
See application file for complete search history.

(56) References Cited

U.S. PATENT DOCUMENTS 5,225,537 A  7/1993  Foster 6,911,323 B2  6/2005  Persson et al.

FOREIGN PATENT DOCUMENTS

| WO | 01/58935 | 8/2001 |
|---|---|---|
| WO | 01/83725 | 11/2001 |
| WO | 02/22776 | 3/2002 |
| WO | 02/077218 | 10/2002 |
| WO | 03/027147 | 4/2003 |
| WO | 03/037932 | 5/2003 |

OTHER PUBLICATIONS

Wells, Biochemistry, vol. 29, pp. 8509-8517, 1990.*
Seffernick et al. J. Bacteriology, vol. 183, pp. 2405-2410, 2001.*
Guo et al. PNAS, vol. 101, No. 25, pp. 9205-9210, 2004.*
Harvey et al. The Journal of Biological Chemistry, vol. 278, No. 10, Mar. 2, 2003, pp. 8363-8369.*
Dickinson, C.D. et al, Proc Natl Acad Sci, vol. 93, pp. 14379-14384 (1996).
Iwanaga, S. et al., Thromb Haemost, vol. 466 (suppl.), Abstract 1474 (1999).
Martin, D.M.A. et al., Biochem., vol. 32, pp. 13949-13955 (1993).

* cited by examiner

*Primary Examiner*—Hope A Robinson
(74) *Attorney, Agent, or Firm*—Len S. Smith

(57) ABSTRACT

The present invention relates to novel human coagulation Factor VII/VIIa proteins having coagulant potential/activity as well as pharmaceutical compositions comprising the proteins, uses thereof, and methods of treatment therewith. In particular, the present invention relates to novel, semi synthetic analogues of human coagulation Factor VII and VIIa (FVII and FVIIa) as well as to a method of their production.

9 Claims, 3 Drawing Sheets

Fig. 1

Ala-Asn-Ala-Phe-Leu-GLA-GLA-Leu-Arg-Pro-Gly-Ser-Leu-GLA-Arg-GLA-Cys-Lys-
                    5                                10                              15

GLA-GLA-Gln-Cys-Ser-Phe-GLA-GLA-Ala-Arg-GLA-Ile-Phe-Lys-Asp-Ala-GLA-Arg-
   20                               25                            30                              35

Thr-Lys-Leu-Phe-Trp-Ile-Ser-Tyr-Ser-Asp-Gly-Asp-Gln-Cys-Ala-Ser-Ser-Pro-
                40                              45                            50

Cys-Gln-Asn-Gly-Gly-Ser-Cys-Lys-Asp-Gln-Leu-Gln-Ser-Tyr-Ile-Cys-Phe-Cys-
55                                60                              65                            70

Leu-Pro-Ala-Phe-Glu-Gly-Arg-Asn-Cys-Glu-Thr-His-Lys-Asp-Asp-Gln-Leu-Ile-
                75                              80                            85                            90

Cys-Val-Asn-Glu-Asn-Gly-Gly-Cys-Glu-Gln-Tyr-Cys-Ser-Asp-His-Thr-Gly-Thr-
                  95                            100                            105

Lys-Arg-Ser-Cys-Arg-Cys-His-Glu-Gly-Tyr-Ser-Leu-Leu-Ala-Asp-Gly-Val-Ser-
    110                              115                            120                          125

Cys-Thr-Pro-Thr-Val-Glu-Tyr-Pro-Cys-Gly-Lys-Ile-Pro-Ile-Leu-Glu-Lys-Arg-
                130                            135                            140

Asn-Ala-Ser-Lys-Pro-Gln-Gly-Arg-Ile-Val-Gly-Gly-Lys-Val-Cys-Pro-Lys-Gly-
145                              150                            155                            160

Glu-Cys-Pro-Trp-Gln-Val-Leu-Leu-Leu-Val-Asn-Gly-Ala-Gln-Leu-Cys-Gly-Gly-
                165                            170                            175                          180

Thr-Leu-Ile-Asn-Thr-Ile-Trp-Val-Val-Ser-Ala-Ala-His-Cys-Phe-Asp-Lys-Ile-
                185                            190                            195

Fig. 1 (continued)

```
Lys-Asn-Trp-Arg-Asn-Leu-Ile-Ala-Val-Leu-Gly-Glu-His-Asp-Leu-Ser-Glu-His-
200               205                 210                 215

Asp-Gly-Asp-Glu-Gln-Ser-Arg-Arg-Val-Ala-Gln-Val-Ile-Ile-Pro-Ser-Thr-Tyr-
        220                 225                 230

Val-Pro-Gly-Thr-Thr-Asn-His-Asp-Ile-Ala-Leu-Leu-Arg-Leu-His-Gln-Pro-Val-
235               240                 245                 250

Val-Leu-Thr-Asp-His-Val-Val-Pro-Leu-Cys-Leu-Pro-Glu-Arg-Thr-Phe-Ser-Glu-
        255                 260                 265                 270

Arg-Thr-Leu-Ala-Phe-Val-Arg-Phe-Ser-Leu-Val-Ser-Gly-Trp-Gly-Gln-Leu-Leu-
                275                 280                 285

Asp-Arg-Gly-Ala-Thr-Ala-Leu-Glu-Leu-Met-Val-Leu-Asn-Val-Pro-Arg-Leu-Met-
        290                 295                 300             305 306

Thr-Gln-Asp-Cys-Leu-Gln-Gln-Ser-Arg-Lys-Val-Gly-Asp-Ser-Pro-Asn-Ile-Thr-
                310                 315                 320

Glu-Tyr-Met-Phe-Cys-Ala-Gly-Tyr-Ser-Asp-Gly-Ser-Lys-Asp-Ser-Cys-Lys-Gly-
325               330                 335                 340

Asp-Ser-Gly-Gly-Pro-His-Ala-Thr-His-Tyr-Arg-Gly-Thr-Trp-Tyr-Leu-Thr-Gly-
        345                 350                 355                 360

Ile-Val-Ser-Trp-Gly-Gln-Gly-Cys-Ala-Thr-Val-Gly-His-Phe-Gly-Val-Tyr-Thr-
                365                 370                 375

Arg-Val-Ser-Gln-Tyr-Ile-Glu-Trp-Leu-Gln-Lys-Leu-Met-Arg-Ser-Glu-Pro-Arg-
        380                 385                 390                 395
```

Fig. 1 (continued)

```
Pro-Gly-Val-Leu-Leu-Arg-Ala-Pro-Phe-Pro
        400              405 406
```

HYBRID MOLECULES HAVING FACTOR VII/VIIA ACTIVITY

CROSS REFERENCE TO RELATED APPLICATIONS

This application is a continuation of International Patent Application PCT/DK2004/000678, filed Oct. 7, 2004, and claims the benefit of priority of U.S. Provisional Patent Application 60/509,849, filed Oct. 9, 2003, and Danish Patent Application PA 2003 01472, filed Oct. 7, 2003.

FIELD OF THE INVENTION

The present invention relates to novel human coagulation Factor VII/VIIa proteins having coagulant potential/activity as well as pharmaceutical compositions comprising the polypeptides, uses and methods of treatment. In particular, the present invention relates to novel, semi synthetic analogues of human coagulation Factor VII and VIIa (FVII and FVIIa) as well as to a method of their production.

BACKGROUND OF THE INVENTION

Blood coagulation is a process consisting of a complex interaction of various blood components (or factors) that eventually gives rise to a fibrin clot. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VIIa).

Initiation of the haemostatic process is mediated by the formation of a complex between tissue factor, exposed as a result of injury to the vessel wall, and Factor VIIa. This complex then converts Factors IX and X to their active forms. Factor Xa converts limited amounts of prothrombin to thrombin on the tissue factor-bearing cell. Thrombin activates platelets and Factors V and VIII into Factors Va and VIIIa, both cofactors in the further process leading to the full thrombin burst. This process includes generation of Factor Xa by Factor IXa (in complex with factor VIIIa) and occurs on the surface of activated platelets. Thrombin finally converts fibrinogen to fibrin resulting in formation of a fibrin clot. In recent years Factor VII and tissue factor have been found to be the main initiators of blood coagulation.

Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa, Factor VIIa or thrombin in vitro. Factor Xa is believed to be the major physiological activator of Factor VII. Like several other plasma proteins involved in haemostasis, Factor VII is, like a number of other coagulation proteins, dependent on Vitamin K for its activity, which is required for the gamma-carboxylation of multiple glutamic acid residues that are clustered close to the amino terminus of the protein. These gamma-carboxylated glutamic acids are required for the metal ion-induced interaction of Factor VII with phospholipids. The conversion of zymogen Factor VII into the activated two-chain molecule occurs by cleavage of an internal $Arg_{152}$-$Ile_{153}$ peptide bond. In the presence of tissue factor, phospholipids and calcium ions, the two-chain Factor VIIa rapidly activates Factor X or Factor IX by limited proteolysis.

Thus, Factor VII has a domain structure comprising a domain rich in γ-carboxyglutamic acid residues (the "GLA domain"), a region containing sequences homologous to human epidermal growth factor, and a catalytic domain containing a serine protease catalytic triad. The catalytic domain is glycosylated in nature.

It is often desirable to stimulate or improve the coagulation cascade in a subject. Factor VIIa has been used to control bleeding disorders that have several causes such as clotting factor deficiencies (e.g. haemophilia A and B or deficiency of coagulation Factors XI or VII) or clotting factor inhibitors. Factor VIIa has also been used to control excessive bleeding occurring in subjects with a normally functioning blood clotting cascade (no clotting factor deficiencies or inhibitors against any of the coagulation factors). Such bleeding may, for example, be caused by a defective platelet function, thrombocytopenia or von Willebrand's disease. Bleeding is also a major problem in connection with surgery and other forms of tissue damage.

FVII can be prepared recombinantly, but the primary structure of Factor VII renders production of the functional protein in prokaryotic host cells impossible, since bacteria do not have the capacity to introduce the vitamin K-dependent γ-carboxylation essential to membrane binding of the protein. Therefore, production of FVII is restricted to expression in higher, mammalian cells. However, expression in mammalian cells is much more complicated and time-consuming than expression in prokaryotes, and the yields are as a rule more limited; in general production in mammalian cells is therefore more expensive than production using prokaryotic host cells.

European Patent No. 200,421 (ZymoGenetics) relates to the nucleotide sequence encoding human Factor VII and the recombinant expression of Factor VII in mammalian cells.

Dickinson et al. (Proc. Natl. Acad. Sci. USA (1996) 93, 14379-14384) relates to a Factor VII variant wherein Leu305 has been replaced by Ala (FVII(Ala305)).

Iwanaga et al. (Thromb. Haemost. (supplement August 1999), 466, abstract 1474) relates to Factor VIIa variants wherein residues 316-320 are deleted or residues 311-322 are replaced with the corresponding residues from trypsin.

Published international patent applications WO 01/83725, WO 02/22776, WO 03/027147, and WO 03/037932 and Danish patent application PA 2002 01423 all relate to variants of Factor VIIa with preserved or increased activity. WO 02/077218 relates to derivatives of Factor VIIa with prolonged serum half-life.

DETAILED DESCRIPTION OF THE INVENTION

The present inventors have realised that it will be feasible to prepare FVII/FVIIa and other proteins having FVII/FVIIa activity, by means of a semi synthetic method, where the γ-carboxyglutamic acid containing lipid membrane binding domain is produced as part of a synthesised polyamino acid that is subsequently ligated to a fragment of FVII produced in prokaryotes that includes at least part of the amino acid sequence of an active FVII catalytic domain.

Such semi synthetic FVII proteins are believed to be novel hybrid proteins, because the bacterially produced part is completely free of native glycosylation, whereas the proteins will include GLA residues that cannot be produced by prokaryotes. It has been found that the glycosylation pattern in the catalytic domain is inessential for the function of FVIIa, so it is believed that these semi synthetic hybrids will share the biological activity/potential of recombinant FVII derived proteins and polypeptides.

Hence, the present invention relates to the novel semi synthetic proteins, as well as to methods for their preparation and use. The present invention also relates to compositions comprising the semi synthetic proteins as well as to methods of treatment and various uses of the novel semi synthetic FVII proteins.

Definitions

In the context of the present specification and claims, a "hybrid molecule" is a molecule that comprises a polypeptide fragment that is typical for protein expression in one type of cells and another polypeptide fragment that is typical for protein expression in a different type of cells, meaning that the hybrid molecule is a non-naturally occurring chemical entity even though it may have an amino acid sequence which is identical to that of a naturally occurring protein.

"Factor VII" (and "FVII") is in the present context intended to denote the polypeptide having the unbroken amino acid sequence set forth in SEQ ID NO: 1, whereas "Factor VIIa" (and "FVIIa") denotes the same polypeptide in processed form, where the peptide bond between R152 and I153 has been cleaved, resulting in a protein having a light chain (residues 1-152 in SEQ ID NO: 1) and a heavy chain (residues 153-406 in SEQ ID NO: 1) that are joined by means of the disulphide bridge between C135 and C262 in SEQ ID NO: 1. The terms also include proteins with a slightly modified amino acid sequence, for instance, a modified N-terminal end including N-terminal amino acid deletions or additions so long as those proteins substantially retain or increase the activity of Factor VIIa. "Factor VII" or "Factor VIIa" within the above definition also includes natural allelic variations that may exist and occur from one individual to another. Also, degree and location of glycosylation or other post-translational modifications may vary depending on the chosen host cells and the nature of the host cellular environment.

The term "Factor VII polypeptide" as used herein means any protein comprising the amino acid sequence 1-406 of native human Factor VII (SEQ ID NO: 1) or variants thereof. This includes but are not limited to human Factor VII, human Factor VIIa and variants thereof.

A "lipid membrane binding domain" is in the present context a protein domain including γ-carboxyglutamic residues and will normally be derived from a vitamin K dependent protein such as thrombin, factors VII, IX, and X; protein C, protein S; osteocalcin, matrix Gla protein, and proline-rich Gla protein 1. Other suitable lipid membrane binding domains are disclosed in U.S. Pat. No. 5,225,537, which is hereby incorporated by reference.

The term "N-terminal Gla-domain" or just "Gla-domain" specifically means the amino acid sequence 1-37 of Factor VII set forth in SEQ ID NO: 1.

The three-letter indication "Gla" means 4-carboxyglutamic acid (γ-carboxyglutamate).

The term "protease domain" means the amino acid sequence 153-406 of Factor VII (the heavy-chain of Factor VIIa).

A "molecule that exhibits bioactivity of human Factor VII/VIIa" means a molecule that, when correctly folded, 1) either is able to convert its substrate Factor X to the active Factor Xa as evidenced by the assays of Examples 1 and/or 2, or 2) which can be converted into such an active molecule when subjected to activation by a substance selected from thrombin, Factor IXa, Factor Xa and Factor XIIa.

According to the present invention, a polyamino acid which is "essentially free of glycosylation" is a polyamino acid where there is substantially no host-cell derived glycosylation of the amino acid residues that form the backbone of the polyamino acid. In one embodiment the polyamino acid is glycosylated at one amino acid. In one embodiment the polyamino acid is glycosylated at two amino acids. In one embodiment the polyamino acid is glycosylated at three amino acids. In one embodiment, there is no glycosylation of these amino acids at all.

The term "substantially the same activity or increased activity compared to recombinant wild type human Factor VIIa", as used herein, means an activity more than 70% of the activity of recombinant wild type human Factor VIIa. In one embodiment the activity is more than 80% of the activity of recombinant wild type human Factor VIIa. In another embodiment the activity is more than 90% of the activity of recombinant wild type human Factor VIIa. In a further embodiment the activity is more than 100% of the activity of recombinant wild type human Factor VIIa. In a further embodiment the activity is more than 120% of the activity of recombinant wild type human Factor VIIa. In a further embodiment the activity is more than 200% of the activity of recombinant wild type human Factor VIIa. In a further embodiment the activity is more than 400% of the activity of recombinant wild type human Factor VIIa.

The term "inherent activity" also includes the ability to generate thrombin on the surface of activated platelets in the absence of tissue factor.

The term "semi synthesis" in the present specification and claims is intended to denote a process for the preparation of a polypeptide that involves both recombinant production of part of the end product and purely chemical synthesis of a different part of the end product, followed by ligation of the two parts to obtain the end product.

The terms "variant" or "variants", as used herein, is intended to designate Factor VII/VIIa having the sequence of SEQ ID NO:1, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "variant" or "variants" within this definition still have FVII activity in its activated, correctly folded form. In one embodiment a variant is 70% identical with the sequence of of SEQ ID NO:1. In one embodiment a variant is 80% identical with the sequence of of SEQ ID NO: 1. In another embodiment a variant is 90% identical with the sequence of of SEQ ID NO:1. In a further embodiment a variant is 95% identical with the sequence of of SEQ ID NO:1.

The term "derivative" as used herein, is intended to designate a hybrid molecule of the invention (i.e. a FVII polypeptide or a variant thereof), in which one or more of the amino acids of the parent peptide have been chemically modified, e.g. by alkylation, PEGylation, acylation, ester formation or amide formation or the like. This includes but are not limited to PEGylated human Factor VIIa, cysteine-PEGylated human Factor VIIa and variants thereof.

The term "polyethylene glycol" or "PEG" means a polyethylene glycol compound or a derivative thereof, with or without coupling agents, coupling or activating moeities (e.g., with thiol, triflate, tresylate, azirdine, oxirane, or preferably with a maleimide moiety). Compounds such as maleimido monomethoxy PEG are exemplary of activated PEG compounds of the invention.

The term "PEGylated hybrid molecule" means a derivative, having a PEG molecule conjugated to an amino acid in the sequence of the hybrid molecule; the term "cysteine-PEGylated hybrid molecule" means that the PEG molecule is conjugated to a sulfhydryl group of a cysteine introduced in the hybrid molecule.

In the present specification and claims, the term "amino acid" denotes any molecule having the formula COOH—CR—NH$_3$, i.e. the term includes within its scope both naturally occurring and non-naturally occurring L- and D-amino acids. In most cases, amino acid manipulation discussed herein will involve use of naturally occurring L-amino acids:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

The term "polyamino acid" denotes a molecule that includes at least 3 amino acid residues.

The term "peptide" denotes a single chain polyamino acid where at least 3 amino acids form up a chain of amino acid residues where the residues are joined via peptide bonds.

An "oligopeptide" is a peptide having at least 10 amino acid residues and at most 99 amino acid residues.

A "polypeptide" is a peptide having at least 100 amino acid residues.

A "protein" is a molecule comprising at least one peptide chain. The molecule may contain several peptide chains that may be associated covalently or non-covalently, it may include unusual amino acids, prosthetic groups, glycosylation, lipidation etc.

The term "vector", as used herein, means any nucleic acid entity capable of the amplification in a host cell of choice. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contain a replication origin and at least one selectable gene, i.e., a gene which encodes a product which is readily detectable or the presence of which is essential for cell growth. The art has provided for both negative and positive selection markers.

The terms "substitution", "insertion", "deletion" and "addition" have the normal, art-recognized meanings when referring to manipulations with amino acid sequences. It should be noted though that when stating that an amino acid in SEQ ID NO: 1 may be substituted with any amino acid residue, this is intended to include substitution with one or more amino acids, i.e. in reality a combination of a substitution and at least one insertion.

The term "subject" as used herein is intended to mean any animal, in particular mammals, such as humans, and may, where appropriate, be used interchangeably with the term "patient".

The term "enhancement of the normal haemostatic system" means an enhancement of the ability to generate thrombin.

General Features of Hybrid Molecules of the Invention

One part of the invention relates to a hybrid molecule exhibiting bioactivity of human Factor VII/VIIa, the hybrid molecule comprising a first polyamino acid capable of forming a functional lipid membrane binding domain comprising at least one γ-carboxyglutamic acid residue, and a second polyamino acid, which is essentially free of glycosylation and which is free of γ-carboxyglutamic acid residues, said second polyamino acid comprising an amino acid sequence capable of forming a functional catalytic domain that exhibits human coagulation Factor VIIa activity at least after the hybrid molecule has been subjected to activation by thrombin, Factor IXa, Factor Xa or Factor XIIa.

When stating that the polyamino acids are "capable of forming" is herein meant that they include the amino acid sequences of the relevant domains, but that the polyamino acids may be in an unfolded or denatured form, meaning that they will have to be refolded in order to attain a biologically active conformation.

Thus, the hybrid molecules of the present invention are either in the form of unactivated Factor VII or in the form of active Factor VIIa, and they may also be inactive due to incorrect folding, as long as correct folding of the hybrid molecule provides for the desired activity. Hence, the novelty of the present hybrid molecules is believed to reside in their primary structure.

Under normal circumstances, a part of the hybrid molecule comprising the first polyamino acid has been prepared by means of chemical peptide synthesis, and a part of the hybrid molecule comprising at least part of the second polyamino acid has been prepared by means of recombinant production in a prokaryotic host cell culture (meaning that, in principle, the part including the first polyamino acid may include some of the second polyamino acid; the parts are then joined by a peptide bond or a bond that mimics the conformation of a peptide bond without adversely affecting the FVII/FVIIa bioactivity of the hybrid molecule; the important characteristic of the hybrid molecule is to preserve a biologically active 3D conformation that provides for the desired FVII/FVIIa activity. Since synthesis of the first polyamino acid is a process where errors will occur with a certain rate, it is of interest to keep the length of the first polyamino acid at a practical minimum and therefore the complete length of the second polyamino acid will normally also be produced by means of recombinant production.

From the above definition of the hybrid molecules of the invention, it is clear that the junction between the first and second polyamino acids is situated C-terminally to the last gla residue in the lipid membrane binding domain and N-terminally to the catalytic domain. It should be noted that the complete hybrid molecule may be produced synthetically, e.g. according to the method disclosed in U.S. Pat. No. 6,326, 468, but it is not the preferred embodiment.

In one embodiments of the invention, the hybrid molecule comprises the complete amino acid sequence of a human FVII polypeptide, i.e. the amino acid sequence set forth in SEQ ID NO: 1, and in that case the first polyamino acid consists of residues 1-37 of SEQ ID NO: 1, and the second polyamino acid consists of residues 153-406 in SEQ ID NO: 1. In the embodiments of the invention where a semi synthetic approach is used in the production of the hybrid molecules, the second part of the hybrid molecule has an N-terminal Cys residue found in SEQ ID NO: 1. In one embodiment, the second part of the hybrid molecule has the amino acid sequence consisting of residues 50-406 of SEQ ID NO: 1 (meaning that the first part of the hybrid molecule consists of residues 1-49 in SEQ ID NO: 1).

In one embodiments of the invention, the junction region between the first and second polyamino acids exclusively comprises amino acids joined by peptide bonds (cf. the discussion below of native chemical ligation) and that this is also the case for the complete hybrid molecule, but it is not excluded to provide hybrid molecules wherein the junction region between the first and second polyamino acids comprises at least one non-peptide bond. Examples of such non-peptide bonds include but are not limited to bonds that result in oxazolidine, oxime, thiazolidine, acylhydrazone, triazole, thioester, or thioether moieties in the junction region between the first and second polyamino acids.

Even though the naturally occurring amino acid sequence set forth in SEQ ID NO: 1 is the most preferred, a number of interesting Factor VII polypeptide variants are also within the scope of the hybrid molecules of the present invention.

Hybrid Molecules with Sequence Variations

In general, any Factor VII/VIIa variant disclosed in any one of WO 01/83725, WO 02/22776, WO 03/027147, WO 03/037932, Danish patent application PA 2002 01423, WO 01/58935 (Maxygen ApS), WO 03/93465 (Maxygen ApS), WO 04/029091 (Maxygen ApS), Dickinson et al. (Proc. Natl. Acad. Sci. USA (1996) 93, 14379-14384), and Iwanaga et al. (Thromb. Haemost. (supplement August 1999), 466, abstract 1474) may be produced as a hybrid molecule of the present invention. Therefore, all of these references are incorporated by reference herein as are any Factor VII/VIIa variants disclosed therein, since they have amino acid sequences that may be identical in the presently dislosed hybrid molecules.

Therefore, in one embodiment of the present invention, the hybrid molecule is one, wherein the catalytic domain comprises the amino acid sequence set forth in SEQ ID NO: 1, amino acid residues 153-406, or a variant of said amino acid sequence that comprises at most 30 modifications selected from single amino acid insertions, single amino acid deletions, single amino acid substations and single amino acid additions. More specifically, the number of substitutions is selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 substitutions, or wherein the number of amino acid insertions is selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 insertions.

The hybrid molecule preferably comprises the amino acid sequence set forth in SEQ ID NO: 1 amino acid residues 153-406, or a variant of said amino acid sequence including at least one of the following modifications:

substitution, independently, of at least one of residues 157-170 with any amino acid residue,
substitution, independently, of at least one of residues 290-339 with any amino acid residue,
substitution of A274 with any amino acid residue,
substitution of S314 with any amino acid residue,
substitution of W364 with any amino acid residue,
substitution of Q366 with any amino acid residue,
substitution of H373 with any amino acid residue,
substitution of F374 with any amino acid residue,
substitution of V376 with any amino acid residue,
deletion of at least one of residues 316-320,
substitution of residues 311-322 with the corresponding residues from trypsin,
substitution of any one of amino acid residues 247-260 and 393-406 with an amino acid that can be chemically conjugated to a bulking agent,
deletion of at least one of amino acid residues 393-406, and addition to the N- or C-terminus of an amino acid that can be conjugated to a bulking agent,
wherein all amino acid numbering conforms with the numbering in SEQ ID NO: 1.

In one embodiment, the hybrid molecule comprises substitution of F374 with any amino acid residue, but especially substitution with Ala, Val, Met, Leu, Trp, Pro, Gly, Ser, Thr, Cys, Asn, Glu, Lys, Arg, His, Asp, Gln, Tyr, and Ile, and in particular with an amino acid residue selected from Pro and Tyr. This particular embodiment can be combined with any one or several of the embodiments described herein.

In a second embodiment the hybrid molecule comprises substitution of A274 with any amino acid residue, such as with an amino acid residue selected from Met, Leu, Lys, and Arg. This particular embodiment can be combined with any one or several of the embodiments described herein.

In a third embodiment the hybrid molecule comprises substitution of L305 with any amino acid residue, such as Ala, Val, Met, Phe, Trp, Pro, Gly, Ser, Thr, Cys, Asn, Glu, Lys, Arg, His, Asp, Gln, Tyr, or Ile, but it is preferred that substitution is made with an amino acid residue selected from the group consisting of Ala, Val, Tyr, and Ile. This particular embodiment can be combined with any one or several of the embodiments described herein.

In a fourth embodiment the hybrid molecule comprises substitution of S314 with any amino acid residue, such as with an amino acid residue selected from the group consisting of Gly, Lys, Gln, and Glu. This particular embodiment can be combined with any one or several of the embodiments described herein.

In a fifth embodiment, the hybrid molecule comprises substitution of K157 with any amino acid residue, such as with an amino acid residue selected from the group consisting of Ala, Gly, Val, Ser, Thr, Asn, Gln, Asp, and Glu. This particular embodiment can be combined with any one or several of the embodiments described herein.

In a sixth embodiment, the hybrid molecule comprises substitution of K337 with any amino acid residue, such as with an amino acid residue selected from the group consisting of Ala, Gly, Val, Ser, Thr, Asn, Gln, Asp, and Glu. This particular embodiment can be combined with any one or several of the embodiments described herein.

In a seventh embodiment, the hybrid molecule comprises substitution of D334 with any amino acid residue, such as with an amino acid residue selected from the group consisting of Ala, Gly and Glu. This particular embodiment can be combined with any one or several of the embodiments described herein.

In an eighth embodiment the hybrid molecule comprises substitution of S336 with any amino acid residue, such as with an amino acid residue selected from the group consisting of Ala, Gly and Glu. This particular embodiment can be combined with any one or several of the embodiments described herein.

In a ninth embodiment, the hybrid molecule comprises substitution of K337 with any amino acid residue, such as with an amino acid residue selected from the group consisting of Ala, Gly, Val, Ser, Thr, Asn, Gln, Asp, and Glu. This particular embodiment can be combined with any one or several of the embodiments described herein.

In a tenth embodiment, the hybrid molecule comprises substitution of V158 with any amino acid residue, such as with an amino acid residue selected from the group consisting of Ala, Ser, Thr, Asn, Gln, Asp, and Glu. This particular embodiment can be combined with any one or several of the embodiments described herein.

In an eleventh embodiment, the hybrid molecule comprises substitution of E296 with any amino acid residue, such as with an amino acid residue selected from the group consisting of Ala, Arg, Lys, Ile, Leu, and Val. This particular embodiment can be combined with any one or several of the embodiments described herein.

In a 12$^{th}$ embodiment, the hybrid molecule comprises substitution of M298 with any amino acid residue, such as with an amino acid residue selected from the group consisting of Ala, Lys, Arg, Gln, and Asn. This particular embodiment can be combined with any one or several of the embodiments described herein.

In a 13$^{th}$ embodiment, the hybrid molecule comprises substitution of R304 with any amino acid residue, such as with an amino acid residue selected from the group consisting of Tyr, Phe, Leu, and Met. This particular embodiment can be combined with any one or several of the embodiments described herein.

A 14$^{th}$ embodiment comprises substitution of M306 with any amino acid residue, such as with an amino acid residue selected from the group consisting of Asp and Asn. This particular embodiment can be combined with any one or several of the embodiments described herein.

A 15$^{th}$ embodiment comprises substitution of D309 with any amino acid residue, such as with an amino acid residue selected from the group consisting of Ser and Thr. This particular embodiment can be combined with any one or several of the embodiments described herein.

A 16$^{th}$ embodiment comprises substitution of S314 with any amino acid residue, such as Gly or Glu, such as with Glu. This particular embodiment can be combined with any one or several of the embodiments described herein.

A 17$^{th}$ embodiment comprises substitution of K316 with any amino acid residue, such as with an amino acid residue selected from the group consisting of Gly, His, Val, Ser, Thr, Asn, Gln, Asp, and Glu, such as with Gln. This particular embodiment can be combined with any one or several of the embodiments described herein.

Any one of the above 17 embodiments can be combined with at least one of the remaining 16 embodiments. In this context reference is made to the claims and to WO 01/83725, WO 02/22776, WO 03/027147, and WO 03/037932 where the possible combinations of the various substitutions are dealt with in detail.

In particular Factor VIIa polypeptide variants wherein the amino acid F374 and at least one amino acid independently selected from the group consisting of residues 157, 305, 314, 337, 334, 336, 158, 296, and 298 of SEQ ID NO:1 are substituted have previously been found to exhibit increased coagulant activity compared to wild type human coagulation Factor VIIa.

The residue F374 is located at the end of an α-helix starting at residue 307. This α-helix is found in the tissue factor-complexed form of Factor VIIa. In free Factor VIIa (Factor VIIa not bound to tissue factor) the helix is distorted and thus possibly unstable. The helix is believed to be important to the activity. The preferred variants according to the present invention may attain the active conformation, which normally has to be induced by tissue factor.

It has been previously found that by replacing the amino acid F374 in combination with one or more of the Lys in position 157 and the Lys in position 337 and the Val in position 158 and the Glu in position 296 and the Met in position 298 and the Asp in position 334 and the Ser in position 336 and the Leu in position 305 and the Ser in position 314, Factor VIIa will spontaneously attain a more active conformation that normally has to be induced by tissue factor.

Therefore, interesting embodiments include
- hybrid molecules comprising at least two substitutions relative to the amino acid sequence of SEQ ID NO:1, wherein said substitutions are substitution of F374, and substitution of one or more amino acids selected from the group consisting of L305, S314, K157, K337, D334, S336, V158, E296, and M298.
- hybrid molecules comprising two substitutions relative to the amino acid sequence of SEQ ID NO:1, wherein said substitutions are substitution of F374 and substitution of one single amino acid selected from the group consisting of L305, S314, K157, K337, D334, S336, V158, E296, and M298.
- hybrid molecules comprising three substitutions relative to the amino acid sequence of SEQ ID NO:1, wherein said substitutions are substitution of F374 and substation of two amino acids selected from the group consisting of L305, S314, K157, K337, D334, S336, V158, E296, and M298.
- hybrid molecules comprising four substitutions relative to the amino acid sequence of SEQ ID NO:1, wherein said substitutions are substitution of F374 and substitution of three amino acids selected from the group consisting of L305, S314, K157, K337, D334, S336, V158, E296, and M298.
- hybrid molecules comprising five substitutions relative to the amino acid sequence of SEQ ID NO:1, wherein said substitutions are substitution of F374 and (ii) substitution of four amino acids selected from the group consisting of L305, S314, K157, K337, D334, S336, V158, E296, and M298.
- hybrid molecules comprising six substitutions relative to the amino acid sequence of SEQ ID NO:1, wherein said substitutions are substitution of F374 and substitution of five amino acids selected from the group consisting of L305, S314, K157, K337, D334, S336, V158, E296, and M298.
- hybrid molecules with seven substitutions relative to the amino acid sequence of SEQ ID NO:1, wherein said substitutions are substitution of F374 and substation of six amino acids selected from the group consisting of L305, S314, K157, K337, D334, S336, V158, E296, and M298.

hybrid molecule with eight substitutions relative to the amino acid sequence of SEQ ID NO:1, wherein said substitutions are substitution of F374 and substitution of seven amino acids selected from the group consisting of L305, S314, K157, K337, D334, S336, V158, E296, and M298.

hybrid molecules with nine substitutions relative to the amino acid sequence of SEQ ID NO:1, wherein said substitutions are substitution of F374 and substitution of eight amino acids selected from the group consisting of L305, S314, K157, K337, D334, S336, V158, E296, and M298.

hybrid molecules with ten substitutions relative to the amino acid sequence of SEQ ID NO:1, wherein said substitutions are substation of F374 and substitution of the amino acids L305, S314, K157, K337, D334, S336, V158, E296, and M298.

In a further aspect, the invention relates to a polynucleotide construct encoding a Factor VII polypeptide comprising at least two substitutions relative to the amino acid sequence of SEQ ID NO: 1, wherein said substitutions are (i) replacement of F374 with any other amino acid, and (ii) replacement with any other amino acid of one or more amino acids selected from the group consisting of L305, S314, K157, K337, D334, S336, V158, E296, and M298.

Also the lipid membrane binding domain of Factor VII may be mutated in a few positions or even substituted with the lipid membrane binding domain of another vitamin K dependent protein in order to provide for a hybrid molecule having a different affinity for cell membranes. The fact that the lipid membrane binding domain is derived from vitamin K dependent protein has the consequence that at least one γ-carboxyglutamic will be present in the first polyamino acid. It is, however, normal that the first polyamino acid comprises a least 2 γ-carboxyglutamic acid residues, such as at least 5, at least 7, at least 9 or at least 10 γ-carboxyglutamic acid residues (in human FVII there are 10 γ-carboxyglutamic acid residues).

In one embodiment the hybrid molecule of the invention includes a lipid membrane binding domain, which is a naturally occurring Gla domain of a vitamin K dependent protein. In one embodiment the hybrid molecule of the invention includes functional variants or fragments of a naturally occurring Gla domain from a vitamin K dependent protein, meaning that the biological activity (membrane binding) is preserved at a satisfactory level. It is preferred that such a functional variant comprises amino acids 1-37 of SEQ ID NO: 1, wherein has been introduced at most 5 amino acid modifications selected from the group consisting of an amino acid addition, deletion, substitution, and insertion. For instance P10 is may be substituted with any amino acid residue, such as an amino acid residue selected from Gln, Arg, His, Asn, and Lys and/or K32 may be substituted with any amino acid residue, such as an amino acid residue selected from Glu, Gln, and Asn. Other amino acids in the Gla domain, based on the different phospholipid affinities and sequences of the vitamin K-dependent plasma proteins, may also be considered for substitution.

In one embodiment the hybrid molecule of the invention comprises a modified Gla-domain as disclosed in WO 99/20767 (University of Minnesota) and WO 00/66753 (University of Minnesota), which references are incorporated by reference herein as are any Factor VII/VIIa variants disclosed therein.

Hybrid Molecules with Prolonged Serum Half-lives

Preferred hybrid molecules of the present invention are derivative that have the same or increased activity compared to wild type Factor VII/VIIa and have increased serum half-lives.

WO 02/077218 and WO 02/02764 discloses derivatives of FVII polypeptides with prolonged serum half-lives. All of these are interesting embodiments of the present invention, and consequently the disclosures of WO 02/077218 and WO 02/02764 is incorporated by reference herein.

Most proteins introduced into the circulation, are cleared quickly from the mammalian subject by the kidneys. This problem may be partially overcome by administering a larger amount of the protein or through repeated administration. However, higher doses of the protein can elicit antibodies which can bind and inactivate the protein and/or facilitate the clearance of the protein from the subject's body. Repeated administration of the therapeutic protein is essentially ineffective and can be dangerous as it can elicit an allergic response.

Various attempts to solve the problems associated with protein therapies include microencapsulation, liposome delivery systems, administration of fusion proteins, and chemical modification. Several of these aim at increasing the molecular weight of the molecule in question because the kidneys are incapable of clearing larger molecules by means of filtration.

In the present specification and claims, this approach is generally referred to as the introduction of a "bulking agent", i.e. a preferably biologically inactive molecular moiety that is attached to the hybrid molecules of the invention with the purpose of increasing the molecular weight of the resulting molecule. The bulking agent may itself provide for the necessary increase, but it may also be a molecular entity that has a high affinity for an abundant serum protein such as albumin.

The most promising of these to date is modification of the therapeutic protein by covalent attachment of polyalkylene oxide polymers, particularly polyethylene glycols (PEG). For example, U.S. Pat. No. 4,179,337 discloses the use of PEG or polypropylene glycol coupled to proteins to provide a physiologically active non-immunogenic water soluble polypeptide composition. Nucci et al. describe several proteins which have been modified by addition of PEG including adenosine deamidase, L-asparaginase, interferon alpha 2b (IFN-α2b), superoxide dismutase, streptokinase, tissue plasminogen activator (tPA), urokinase, uricase, hemoglobin, interleukins, interferons, TGF-beta, EGF, and other growth factors (Nucci et al., 1991, *Adv. Drug Delivery Rev.* 4:133-151). Attempts such as these have resulted in somewhat longer half-life of the proteins and reduction of protein immunogenicity.

Typically, PEGylation of proteins involves activating PEG with a functional group which will react with lysine residues on the surface of the protein. If the modification of the protein goes to completion, the activity of the protein is usually lost. Modification procedures which allow partial PEGylation of the protein usually result in only about 50% loss of activity and greatly increased serum half-life, so that the overall effective dose of the protein is lower.

Recent developments in protein PEGylation methods employ activated PEG reagents which react with thiol groups of the protein, resulting in covalent attachment of PEG to a cysteine, which residue was inserted in place of a naturally occurring lysine of the protein. Shaw et al. (U.S. Pat. No. 5,166,322) describe specific variants of IL-3 which have a cysteine introduced at specific sites within the naturally occurring amino acid sequence. Sulfhydryl reactive compounds (e.g. activated polyethylene glycol) are then attached to these cysteines by reaction with the IL-3 variant. Katre et al. (U.S. Pat. No. 5,206,344) describe specific IL-2 variants which contain a cysteine introduced at a specific site within the naturally occurring amino acid sequence. The IL-2 variant is subsequently reacted with an activated polyethylene glycol reagent to attach this moiety to a cysteine.

The following discussion focuses on PEG as a bulking agent, but it should be noted that the present invention is not limited in its scope to the use of PEG. Other possibilities include introduction of other polymers than PEG (cf. below), excess glycosylation, or coupling to a fatty acid or a lipid.

Areas in the Factor VIIa molecule have previously been identified where changes to the primary structure as well as other modifications are allowed without influencing or reducing the biological activity of Factor VIIa—the same areas are relevant for introducing modification in the hybrid molecules of the present invention. The areas within the structure of Factor VIIa, which have been identified not to be involved in the binding to tissue factor or to Factor X, includes the amino acid positions from 247-260 and from 393-406 of SEQ ID NO: 1. Specifically the amino acids in positions Q250, R396, and P406 of the sequence of SEQ ID NO: 1, have been analysed for the introduction of cysteine (Cys) residues. The introduction of a Cys residues is followed by the conjugation with a chemical group such as a bulking agent, e.g. polyethylene glycol (PEG) in order to increase the half-life in circulation of the Factor VII derivative. A cysteine has also been introduced in the C-terminal sequence of SEQ ID NO: 1 (referred to as 407C), which is followed by the conjugation of PEG. Also this addition of a cysteine in the C-terminal sequence of SEQ ID NO: 1 is without reduction in proteolytic activity of Factor VIIa polypeptides. These Factor VII derivatives, e.g. a Factor VII polypeptide conjugated with a PEG molecule, are therapeutically useful in situations where a prolonged effect of Factor VII polypeptides is desirable, e.g. in situations where repeated administration or administration of a larger amount of the Factor VII polypeptide is inconvenient or problematic. Furthermore, the hybrid molecules with introduced amino acids (e.g. a Cys residue) capable of being conjugated with a chemical group at positions in the Factor VIIa molecule, which do no influence the proteolytic activity, may be used to introduce any functional group of a conjugate of Factor VII.

Preferably the chemical group is a biocompatible, non-toxic, non-immunogenic and water-soluble polymer. Preferably the chemical group is water-soluble in all proportions.

Therefore, interesting embodiments of the invention include that an amino acid residue (preferably Cys) is inserted corresponding to any one of positions 247-260 or 393-405 in SEQ ID NO: 1 or wherein said amino acid residue is added to an amino acid corresponding to the N- or C-terminal amino acid of SEQ ID NO: 1. The amino acid residue may be added to an amino acid corresponding to the C-terminal amino acid residue of SEQ ID NO: 1. According to the present invention, a bulking agent is preferably coupled to said amino acid residue.

Also, the present invention relates to hybrid molecules comprising the amino acid sequence of SEQ ID NO: 1 or a variant thereof as discussed above, wherein an amino acid has been substituted with a different amino acid, wherein the different amino acid is capable of being conjugated to a chemical group and wherein the hybrid molecule has substantially the same activity or increased activity compared to recombinant wild type human Factor VIIa.

An amino acid at a position selected from 247-260, 393-405 or 406 of SEQ ID NO: 1 may therefore be substituted with any amino acid. It is to be understood that any amino acid at a position selected from 247-260, 393-405 or 406 of SEQ ID NO: 1 can be substituted without substantially reduction in activity of the Factor VII polypeptide. It is preferred to substitute an amino acid corresponding to an amino acid selected from R396, Q250 or P406 of SEQ ID NO: 1 in the hybrid molecule of the invention comprising SEQ ID NO: 1 or in a variant thereof discussed above. An especially preferred embodiment includes that R396 is substituted with any amino acid residue. An equally preferred embodiment includes that Q250 is substituted with any amino acid residue and it is also preferred that P406 is substituted with any amino acid residue. As for the "insertion embodiments" the preferred substituting amino acid is a Cys.

The amino acid substitution, insertion, or addition, and subsequent conjugation with a bulking agent is without substantial reduction of procoagulant activity of the activated form of the Factor VII derivative compared with recombinant wild type human Factor VIIa, cf. the assays described in Examples 1 and 2.

It is to be understood that the amino acid replacing the amino acid in or being inserted into or being added to the hybrid molecule is capable of being conjugated with any chemical group that will increase the actual molecular weight of the hybrid molecule (i.e. a bulking agent). This conjugation with the chemical group includes but is not limited to covalent attachment of polyethylene glycol (PEG), monomethoxy-polyethylene glycol, dextran, poly-(N-vinyl pyrrolidone) polyethylene glycol, propylene glycol homopolymers, a polypropylene oxide/ethylene oxide co-polymer, polypropylene glycol, polyoxyethylated polyols (e.g., glycerol) and polyvinyl alcohol, colominic acids or other carbohydrate based polymers, polymers of amino acids, and biotin derivatives.

Embodiments of the hybrid molecules include derivatives comprising a hybrid molecule of the invention having the amino acid sequence of SEQ ID NO: 1 or a variant thereof, wherein an amino acid has been substituted with a different amino acid, wherein the different amino acid is conjugated with a chemical group that increases the actual molecular weight of the hybrid molecule with 300-100,000 daltons and wherein the hybrid molecule has substantially the same activity or increased activity compared to recombinant wild type human Factor VIIa.

Other Hybrid Molecules

Apart from the above-described molecules of the invention, a different class of hybrid molecules that include inactivating modifications in the catalytic center are also contemplated in the present invention. These include the inactive variants disclosed in WO 02/077218.

That is, these hybrid molecules share all other features with the hybrid molecules of the invention, but they include modifications that render the catalytic site substantially inactive.

In a further aspect, the invention therefore relates to another class of hybrid molecules, that are produced according to the same principles set forth above, wherein a Factor VII polypeptide is further modified in its catalytic center, which modification inhibits the ability of the Factor VII polypeptide to activate plasma Factor X or IX. In one embodiment the inactivated Factor VII polypeptide is modified in its catalytic center with a serine protease inhibitor. In a further embodiment the inactivated Factor VII polypeptide is modified in its catalytic center with a peptide halomethyl ketone selected from the group consisting of: Phe-Phe-Arg chloromethyl ketone, Phe-Phe-Arg chloromethylketone, D-Phe-Phe-Arg chloromethyl ketone, D-Phe-Phe-Arg chloromethylketone Phe-Pro-Arg chloromethylketone, D-Phe-Pro-Arg chloromethylketone, Phe-Pro-Arg chloromethylketone, D-Phe-Pro-Arg chloromethylketone, L-Glu-Gly-Arg chloromethylketone and D-Glu-Gly-Arg chloromethylketone, Dansyl-Phe-Phe-Arg chloromethyl ketone, Dansyl-Phe-Phe-Arg chloromethylketone, Dansyl-D-Phe-Phe-Arg chloromethyl ketone, Dansyl-D-Phe-Phe-Arg chloromethylketone, Dansyl-Phe-Pro-Arg chloromethylketone, Dansyl-D-Phe-Pro-Arg chloromethylketone, Dansyl-Phe-Pro-Arg chloromethylketone, Dansyl-D-Phe-Pro-Arg chloromethylketone, Dansyl-L-Glu-Gly-Arg chloromethylketone and Dansyl-D-Glu-Gly-Arg chloromethylketone.

The term "inactivated Factor VII polypeptide" as used herein means a Factor VII polypeptide with no ability to activate plasma Factor X or IX.

In a further aspect, the invention relates to a hybrid molecule in the form of an inactivated Factor VII derivative, wherein an inactivated Factor VII polypeptide comprising the amino acid sequence of SEQ ID NO: 1 or a variant thereof and having a modification in its catalytic center, which modification inhibits the ability of the Factor VII polypeptide to activate plasma Factor X or IX, is further conjugated with a chemical group that increases the actual molecular weight of the inactivated Factor VII polypeptide with about 300 daltons to about 100,000 daltons, i.e. molecules that include a bulking agent.

In a further aspect, the invention relates to an inactivated hybrid molecule in the form of a Factor VII derivative, wherein an inactivated Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated with a chemical group and wherein the inactivated FVII polypeptide including a modification in its catalytic center, which modification inhibits the ability of the Factor VII polypeptide to activate plasma Factor X or IX, further includes a bulking agent.

In a further aspect, the invention relates to a hybrid molecule in the form of an inactivated Factor VII derivative, wherein an inactivated Factor VII polypeptide comprising the amino acid sequence of SEQ ID NO: 1 or a variant thereof, wherein an amino acid corresponding to an amino acid at a position selected from 247-260, 393-405 or 406 of SEQ ID NO: 1 has been substituted with a different amino acid and having a modification in its catalytic center, which modification inhibits the ability of the Factor VII polypeptide to activate plasma Factor X or IX, is further conjugated to a bulking agent.

In a further aspect, the invention relates to a hybrid molecule in the form of an inactivated Factor VII derivative, wherein an inactivated Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid and having a modification in its catalytic center, which modification inhibits the ability of the Factor VII polypeptide to activate plasma Factor X or IX, is further conjugated to a bulking agent.

In a further aspect, the invention relates to a hybrid molecule in the form of an inactivated Factor VII derivative, wherein an inactivated Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated to a bulking agent.

In a further aspect, the invention relates to a hybrid molecule in the form of an inactivated Factor VII derivative, wherein an inactivated Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof and having a modification in its catalytic center, which modification inhibits the ability of the Factor VII polypeptide to activate plasma Factor X or IX, is further conjugated to a bulking agent.

In a further aspect, the invention relates to a composition comprising a hybrid molecule in the form of an inactivated Factor VII derivative, wherein an inactivated Factor VII polypeptide comprising the amino acid sequence of SEQ ID NO: 1 or a variant thereof and having a modification in its catalytic center, which modification inhibits the ability of the Factor VII polypeptide to activate plasma Factor X or IX is further conjugated to a bulking agent; and optionally, a pharmaceutically acceptable carrier.

In a further aspect, the invention relates to a composition comprising a hybrid molecule in the form of an inactivated Factor VII derivative, wherein an inactivated Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated to a bulking agent; and optionally, a pharmaceutically acceptable carrier.

In a further aspect, the invention relates to a composition comprising a hybrid molecule in the form of an inactivated Factor VII derivative, wherein an inactivated Factor VII polypeptide comprising the amino acid sequence of SEQ ID NO: 1 or a variant thereof, wherein an amino acid corresponding to an amino acid at a position selected from 247-260, 393-405 or 406 of SEQ ID NO: 1 has been substituted with a different amino acid and having a modification in its catalytic center, which modification inhibits the ability of the Factor VII polypeptide to activate plasma Factor X or IX, is further conjugated to a bulking agent; and optionally, a pharmaceutically acceptable carrier.

In a further aspect, the invention relates to a composition comprising a hybrid molecule in the form of an inactivated Factor VII derivative, wherein an inactivated Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid and having a modification in its catalytic center, which modification inhibits the ability of the Factor VII polypeptide to activate plasma Factor X or IX, is further conjugated to a bulking agent; and optionally, a pharmaceutically acceptable carrier.

In a further aspect, the invention relates to a composition comprising a hybrid molecule in the form of an inactivated Factor VII derivative, wherein an inactivated Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated to a bulking agent; and optionally, a pharmaceutically acceptable carrier.

In a further aspect, the invention relates to a composition comprising a hybrid molecule in the form of an inactivated Factor VII derivative, wherein an inactivated Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof and having a modification in its catalytic center, which modification inhibits the ability of the Factor VII polypeptide to activate plasma Factor X or IX, is further conjugated to a bulking agent; and optionally, a pharmaceutically acceptable carrier.

In a further aspect, the invention relates to a pharmaceutical composition comprising a hybrid molecule in the form of an inactivated Factor VII derivative, wherein an inactivated Factor VII polypeptide comprising the amino acid sequence of SEQ ID NO: 1 or a variant thereof and having a modification in its catalytic center, which modification inhibits the ability of the Factor VII polypeptide to activate plasma Factor X or IX is further conjugated to a bulking agent; and optionally, a pharmaceutically acceptable carrier; and optionally, a pharmaceutically acceptable carrier.

In a further aspect, the invention relates to a pharmaceutical composition comprising a hybrid molecule in the form of an inactivated Factor VII derivative, wherein an inactivated Factor VII polypeptide comprising the amino acid sequence of SEQ ID NO: 1 or a variant thereof, wherein an amino acid has been substituted with a different amino acid, wherein the different amino acid is capable of being conjugated with a chemical group and wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated to a bulking agent; and optionally, a pharmaceutically acceptable carrier.

In a further aspect, the invention relates to a pharmaceutical composition comprising a hybrid molecule in the form of an inactivated Factor VII derivative, wherein an inactivated Factor VII polypeptide comprising the amino acid sequence of SEQ ID NO: 1 or a variant thereof, wherein an amino acid corresponding to an amino acid at a position selected from 247-260, 393-405 or 406 of SEQ ID NO: 1 has been substituted with a different amino acid and having a modification in its catalytic center, which modification inhibits the ability of the Factor VII polypeptide to activate plasma Factor X or IX, is further conjugated to a bulking agent; and optionally, a pharmaceutically acceptable carrier.

In a further aspect, the invention relates to a pharmaceutical composition comprising a hybrid molecule in the form of an inactivated Factor VII derivative, wherein an inactivated Factor VII polypeptide comprising the amino acid sequence of SEQ ID NO: 1 or a variant thereof, wherein an amino acid corresponding to an amino acid selected from R396, Q250 or P406 of SEQ ID NO: 1 has been substituted with a different amino acid and having a modification in its catalytic center, which modification inhibits the ability of the Factor VII polypeptide to activate plasma Factor X or IX, is further conjugated to a bulking agent; and optionally, a pharmaceutically acceptable carrier.

In a further aspect, the invention relates to a pharmaceutical composition comprising a hybrid molecule in the form of an inactivated Factor VII derivative, wherein an inactivated Factor VII polypeptide comprising the amino acid sequence of SEQ ID NO: 1 or a variant thereof, wherein an amino acid capable of being conjugated with a chemical group has been inserted within the sequence of SEQ ID NO: 1 or a variant thereof at a position, wherein the Factor VII polypeptide has substantially the same activity or increased activity compared to recombinant wild type human Factor VIIa and having a modification in its catalytic center, which modification inhibits the ability of the Factor VII polypeptide to activate plasma Factor X or IX, is further conjugated a bulking agent; and optionally, a pharmaceutically acceptable carrier.

In a further aspect, the invention relates to a pharmaceutical composition comprising a hybrid molecule in the form of an inactivated Factor VII derivative, wherein an inactivated Factor VII polypeptide comprising the amino acid sequence of SEQ ID NO: 1 or a variant thereof, wherein an amino acid capable of being conjugated with a chemical group has been added to the N- or C-terminal of SEQ ID NO: 1 or a variant thereof and having a modification in its catalytic center, which modification inhibits the ability of the Factor VII polypeptide to activate plasma Factor X or IX, is further conjugated to a bulking agent; and optionally, a pharmaceutically acceptable carrier.

These inactivated hybrid molecules are interesting in a large number of clinical indications that are described in detail in WO 02/077218, and all of these indications are also part of the present invention insofar as it relates to such inactivated hybrid molecules.

Preparation of the Hybrid Molecules of the Invention

The present invention also includes as an important aspect, a method for preparation of a hybrid molecule exhibiting human coagulation Factor VII or VIIa activity, the method comprising
(a) synthesising, by means of peptide synthesis, a first polyamino acid, which comprises the amino acid sequence of a functional membrane binding domain derived from a vitamin K-dependent protein,
(b) producing and recovering, from a culture of recombinant cells, a second polyamino acid, which is free of Gla residues and which includes at least part of an amino acid sequence that constitutes a catalytic domain having human Factor VII/VIIa activity,
(c) joining the products of steps (a) and (b) to produce a third polyamino acid, wherein an N-terminus is the N-terminus of the product of step (a), and wherein the third polyamino acid includes an amino acid sequence that constitutes a catalytic domain having human Factor VII/VIIa activity,
(d) recovering the product of step (c).

Depending on the type of ligation chosen for the joining step c, it may be necessary to refold the end-product. Also, if the end-product is intended to a hybrid molecule with increased serum half-life, a further step may include coupling of the hybrid molecule to a bulking agent. It will be understood, that the refolding procedure, if necessary at all, may be performed both before and after the coupling to a bulking agent.

For the purpose of recombinant expression in step b, the nucleic acid fragments encoding the second polyamino acid will normally be inserted in suitable vectors to form cloning or expression vectors carrying the nucleic acid fragments of the invention. Details concerning the construction of these vectors of the invention will be discussed in context of transformed cells and microorganisms below. The vectors can be in the form of plasmids, phages, cosmids, or mini-chromosomes. Preferred cloning and expression vectors used in the invention are capable of autonomous replication, thereby enabling high copy-numbers for the purposes of high-level expression or high-level replication for subsequent cloning.

The general outline of a vector for use in the of the invention comprises the following features in the 5'→3' direction and in operable linkage: a promoter for driving expression of the nucleic acid fragment encoding the second polyamino acid, optionally a nucleic acid sequence encoding a leader peptide enabling secretion (to the extracellular phase or, where applicable, into the periplasm) of or integration into the membrane of the second polyamino acid, the nucleic acid fragment of the invention, and optionally a nucleic acid sequence encoding a terminator. When operating with expression vectors in producer strains or cell-lines it is for the purposes of genetic stability of the transformed cell preferred that the vector when introduced into a host cell is integrated in the host cell genome.

The vectors of the invention are used to transform host cells to produce the second polyamino acid. Such transformed cells can be cultured cells or cell lines used for propagation of the nucleic acid fragments and vectors encoding the second polyamino acod or used for recombinant production of second polyamino acid.

Preferred transformed cells of the invention are microorganisms such as bacteria (such as the species *Escherichia* [e.g. *E. coli*], *Bacillus* [e.g. *Bacillus subtilis*], or *Salmonella*, yeasts (such as *Saccharomyces cerevisiae*), and protozoans. Alternatively, the transformed cells are derived from a multicellular organism such as a fungus, an insect cell, a plant cell, or a mammalian cell.

Prokaryotic host cells, including strains of the bacteria *Escherichia coli*, *Bacillus* and other genera are the most useful host cells within the present invention. Techniques for transforming these hosts and expressing foreign DNA sequences cloned therein are well known in the art (see, e.g., Sambrook et al., ibid.). When expressing DNA encoding a second polyamino acid in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the polypeptide, thereby obviating the need for denaturation and refolding. Methods for producing heterologous disulfide bond-containing polypeptides in bacterial cells are disclosed by Georgiou et al., U.S. Pat. No. 6,083,715.

For the purposes of cloning and/or optimized expression it is preferred that the transformed cell is capable of replicating the nucleic acid fragment encoding the second polyamino acid. To ultimately produce the second polyamino acid, transformed cells must express the nucleic acid fragment encoding the first polyamino acid. It is convenient, although far from essential, that the expression product is either exported out into the culture medium or carried on the surface of the transformed cell.

When an effective producer cell has been identified it is preferred, on the basis thereof, to establish a stable cell line which carries the which expresses the nucleic acid fragment encoding the second polyamino acid. Preferably, this stable cell line secretes or carries on its surfaces the second polyamino acid, thereby facilitating purification thereof.

In general, plasmid vectors containing replicon and control sequences which are derived from species compatible with the host cell are used in connection with the hosts. The vector ordinarily carries a replication site, as well as marking sequences which are capable of providing phenotypic selection in transformed cells. For example, *E. coli* is typically transformed using pBR322, a plasmid derived from an *E. coli* species. The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the prokaryotic microorganism for expression.

Those promoters most commonly used in prokaryotic recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EP-A-0 036 776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes may be expressed efficiently in *E. coli* from their own promoter sequences, precluding the need for addition of another promoter by artificial means.

In addition to prokaryotes, eukaryotic microbes, such as yeast cultures may also be used, and here the promoter should be capable of driving expression. *Saccharomyces cerevisiase*, or common baker's yeast is the most commonly used among eukaryotic microorganisms, although a number of other strains are commonly available. For expression in *Saccharomyces*, the plasmid YRp7, for example, is commonly used. This plasmid already contains the trpl gene which provides a selection marker for a mutant strain of yeast lacking the ability to grow in tryptophan for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293, *Spodoptera frugiperda* (SF) cells (commercially available as complete expression systems from i.a. Protein Sciences, 1000 Research Parkway, Meriden, Conn. 06450, U.S.A. and from Invitrogen), and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

The peptide synthesis in step (a) is selected from solid phase and liquid phase peptide synthesis, but it is preferred to use solid phase peptide synthesis.

Such methods are known in the art. Solid phase synthesis of peptides has been known for 40 years following the pioneering work of Merrifield first published in 1962. The general principle of this type of synthesis is as follows:

(a) An N-protected amino acid (the protecting group is commonly t-butoxycarbonyl, abbreviated to Boc) is attached to a solid, non-soluble support (commonly a polystyrene resin) at its carboxylic end via a linking group (commonly a benzyl ester).

(b) The N-protecting group is removed by means which do not detatch the amino acid from the solid support, and a second N-protected amino acid is coupled to the one already attached (commonly by use of a carbodi-imide coupling agent).

(c) The sequence is repeated using as many N-protected amino acids as are required until the desired peptide has been formed, still attached at its carboxyl end to the solid support.

(d) The final N-protecting group is removed and the peptide is separated from the solid support by cleavage of the linking group (commonly by use of a strong acid).

The whole synthesis can be machine-aided and in some circumstances the peptide may be formed without manual intervention. The Boc protecting groups are removed by trifluoroacetic acid and the peptide chain is removed from the solid support with a stronger acid such as hydrofluoric acid.

Since the introduction of this technique many modifications have been introduced, but the process generally used today is essentially as first described. Two major innovations have been the use of a polyamide as the solid support and the use of a N-fluoren-9-ylmethoxycarbonyl (Fmoc) protecting group for the N-α-group of the amino acid. The Fmoc group is distinguished by being labile to base (commonly piperidine). For further detail reference is made, for example, to Atherton and Sheppard, "Solid phase peptide synthesis—a practical approach", IRL Press at Oxford University Press, 1989; Barany et al., "Solid-phase peptide synthesis: a silver anniversary report", Int. J. Peptide Protein Res., 1987, 30, 705-739 and Fields et al., ibid, 1990, 35, 161-214.

U.S. Pat. No. 6,326,468 discloses a convenient method for the preparation of very long polypeptides by means of solid phase synthesis in an aqueous environment. The contents thereof are therefore incorporated by reference herein. However, the present invention aims at a simplification of the procedure described in U.S. Pat. No. 6,326,468, in the sense that only one single ligation is necessary when using the preferred embodiment of the present invention.

The disclosure of U.S. Pat. No. 6,326,468 relies mainly on a combination of the above referenced traditional solid phase peptide synthesis with native chemical ligation, i.e. a chemoselective reaction involving ligation of a first unprotected amino acid, peptide or polypeptide and a second unprotected amino acid, peptide or polypeptide resulting in the formation of an amide bond having a backbone structure indistinguishable from that of a peptide or polypeptide occurring in nature or via recombinant expression.

In U.S. Pat. No. 6,326,468, this joining of to peptides is achieved by reacting a peptide having a thioester at the C-terminus with a peptide having a cysteine at the N-terminus, thereby obtaining a native peptide binding. Hence, in terms of the present invention, this technology can be used by excisting step (c) referred to above in the following manner:

1) binding or having the product of step (a), which is in the form of a partially or completely unprotected first peptide segment, to a solid phase via a linker to form a solid phase-bound first peptide segment, wherein said partially or completely unprotected first peptide segment comprises an N-terminus and a thioester of the formula —COSR at its C-terminus, wherein said linker comprises a cleavable moiety and said partially or completely unprotected first peptide segment is bound to said linker at said N-terminus, and wherein R is a straight or branched $C_{1-15}$ functionalized alkyl group, a $C_{1-15}$ aromatic structure, or 1 to 4 amino acids or derivatives thereof;

2) ligating the product of step (b), which is in the form of a partially or completely unprotected second peptide segment, to said solid phase-bound first peptide segment and optionally removing some or all protection groups, wherein said second peptide segment comprises a cysteine at its N-terminus, and wherein said N-terminal cysteine of said second peptide segment is capable of selectively ligating to said C-terminus of said solid phase-bound first peptide, to form the hybrid molecule in the form of a solid phase-bound peptide.

Alternatively, step (c) comprises 1) binding or having the product of step (b), which is in the form of a partially or completely unprotected first peptide segment, to a solid phase via a linker, wherein said first peptide segment comprises an N-terminal cysteine and a C-terminal residue capable of binding to said linker, wherein said linker comprises a cleavable moiety and said first peptide segment is bound to said linker at said C-terminal residue;
2) ligating the product of step (a), which is in the form of a partially or completely unprotected second peptide segment, to said solid phase-bound first peptide segment and optionally removing some or all protection groups, wherein said second peptide segment comprises a thioester at its C-terminus, and wherein said C-terminal thioester of said second peptide segments binds to said N-terminal cysteine of said solid phase-bound first peptide segment to form to form the hybrid molecule in the form of a solid phase-bound peptide.

The product of step (a) comprises the amino acid sequence of the lipid membrane binding domain of a vitamin K dependent protein and terminates C-terminally to the last γ-carboxyglutamic acid in said amino acid sequence, and the product of step (b) comprises the amino acid sequence of the catalytic site of a protein having Factor VII/VIIa activity and terminates N-terminally with a cysteine residue.

In one preferred embodiment, the product of step (a) consists of amino acids 1-49 in SEQ ID NO: 1, wherein Q49 has been replaced with a corresponding thioester. In another preferred embodiment the product of step (b) consists of amino acids 50-406 in SEQ ID NO: 1.

The solid phase may be any material having a surface which is substantially insoluble when exposed to organic or aqueous solutions used for coupling, deprotecting, and cleavage reactions. Examples of solid phase materials include glass, polymers and resins, including polyacrylamide, PEG, polystyrene PEG-A, PEG-polystyrene, macroporous, POROS™, cellulose, reconstituted cellulose (e.g. Perloza), nitrocellulose, nylon membranes, controlled-pore glass beads, acrylamide gels, polystyrene, activated dextran, agarose, polyethylene, functionalized plastics, glass, silicon, aluminum, steel, iron, copper, nickel and gold. Such materials may be in the form of a plate, sheet, petri dish, beads, pellets, disks, or other convenient forms.

One drawback associated with the above-referenced native ligation method is the fact that it has to be done under reducing conditions, meaning that all disulphide bridges in the hybrid molecule of the invention will be broken, and hence the product will be denatured. Therefore, the native ligation process necessitates a subsequent refolding step performed under oxidizing conditions.

A convenient method for refolding is set forth in Example 3, but it is also possible to utilise the refolding schemes of U.S. Pat. No. 5,739,281, i.e. a cyclic refolding strategy. In the present context, there should be no need for the inclusion of an affinity handle in the hybrid molecule, because it will already be bound to a solid phase via a cleavable linker so the refolding schemes of U.S. Pat. No. 5,739,281 will be applicable directly to the solid-phase bound end-product of the presently dislosed process.

Generally applicable methods for refolding of proteins are described in "Refolding of therapeutic proteins produced in Escherichia coli as inclusion bodies", S. Misawa and I. Kumagai, *Biopolymers*, 1999, 51, 297-307.

However, if it is desired to avoid the subsequent steps of refolding, alternatives to the native chemical ligation process described above are known in the art:

Oxazolidine chemical ligation: Chemoselective reaction involving ligation of a first unprotected amino acid, peptide or polypeptide having an aldehyde or ketone moiety and a second unprotected amino acid, peptide or polypeptide having a 1-amino, 2-ol moiety resulting in the formation of an oxazolidine moiety at the ligation site. The backbone structure of a peptide or polypeptide product resulting from oxazolidine forming chemical ligation is distinguishable from that of a peptide or polypeptide occurring in nature or via recombinant expression.

Oxime chemical ligation: Chemoselective reaction involving ligation of a first unprotected amino acid, peptide or polypeptide having an amino-oxy moiety and a second unprotected amino acid, peptide or polypeptide having an aldehyde or ketone moiety resulting in the formation of an oxime moiety at the ligation site. The backbone structure of a peptide or polypeptide product resulting from oxime chemical ligation is distinguishable from that of a peptide or polypeptide occurring in nature or via recombinant expression. This type of ligation is disclosed in "Facile synthesis of homogeneous artificial proteins", K. Rose, *Journal of the American Chemical Society*, 1994, 116, 30-33, and also in "A fluorescent interleukin-8 receptor probe produced by targeted labeling at the amino-terminus", S. Alouani, H. F. Gaertner, J. J. Mermod, C. A. Power, K. B. Bacon, T. N. C. Wells, and A. E. I. Proudfoot, *European Journal of Biochemistry*, 1995, 227, 328-334.

Thiazolidine chemical ligation: Chemoselective reaction involving ligation of a first unprotected amino acid, peptide or polypeptide having an aldehyde or ketone moiety and a second unprotected amino acid, peptide or polypeptide having a 1-amino, 2-thiol moiety resulting in the formation of a thiazolidine moiety at the ligation site. The backbone structure of a peptide or polypeptide product resulting from thiazolidine chemical ligation is distinguishable from that of a peptide or polypeptide occurring in nature or via recombinant expression.

Acylhydrazone chemical ligation: Chemoselective reaction involving ligation of a first unprotected amino acid, peptide or polypeptide and a second unprotected amino acid, peptide or polypeptide resulting in the formation of an acylhydrazone bond at the ligation site. The backbone structure of a peptide or polypeptide product resulting from acylhydrazone chemical ligation is distinguishable from that of a peptide or polypeptide occurring in nature or via recombinant expression.

Triazole chemical ligation: Chemoselective reaction involving ligation of a first unprotected amino acid, peptide or polypeptide and a second unprotected amino acid, peptide or polypeptide resulting in the formation of a triazole bond at the ligation site. The backbone structure of a peptide or polypeptide product resulting from triazole chemical ligation is distinguishable from that of a peptide or polypeptide occurring in nature or via recombinant expression.

Thioester chemical ligation: Chemoselective reaction involving ligation of a first unprotected amino acid, peptide or polypeptide and a second unprotected amino acid, peptide or polypeptide resulting in the formation of a thioester bond at the ligation site. The backbone structure of a peptide or polypeptide product resulting from thioester chemical ligation is distinguishable from that of a peptide or polypeptide occurring in nature or via recombinant expression.

Thioether chemical ligation: Chemoselective reaction involving ligation of a first unprotected amino acid, peptide or polypeptide and a second unprotected amino acid, peptide or polypeptide resulting in the formation of a thioether bond at the ligation site. The backbone structure of a peptide or polypeptide product resulting from thioether chemical ligation is distinguishable from that of a peptide or polypeptide occurring in nature or via recombinant expression.

It will be unproblematic for the skilled person to select suitable fragments of the hybrid molecule that can include the first polyamino acid and the second polyamino acid.

The recombinantly produced part of the hybrid molecules of the invention may be produced by means of recombinant nucleic acid techniques. In general, a cloned wild-type Factor VII nucleic acid sequence is modified to encode the desired protein when a variant is produced. The sequence is then inserted into an expression vector, which is in turn transformed or transfected into prokaryotic host cells. The complete nucleotide and amino acid sequences for human Factor VII are known (see U.S. Pat. No. 4,784,950).

The amino acid sequence alterations (when relevant) may be accomplished by a variety of techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of Factor VII, one may introduce the alteration(s) of choice. Likewise, procedures for preparing a DNA construct using polymerase chain reaction using specific primers are well known to persons skilled in the art (cf. PCR Protocols, 1990, Academic Press, San Diego, Calif., USA).

The nucleic acid construct encoding the recombinantly produced part of a hybrid moleucle of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed. Cold Spring Harbor Laboratory, Cold Spring Harbor, N.Y., 1989).

The nucleic acid construct may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e.g. in an automatic DNA synthesiser, purified, annealed, ligated and cloned in suitable vectors. The DNA sequences may also be prepared by polymerase chain reaction using specific primers, for instance as described in U.S. Pat. No. 4,683,202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct is preferably a DNA construct. DNA sequences for use in producing hybrid molecules according to the present invention will typically be manipulated as described above for bacterial expression.

As will be appreciated by those skilled in the art, additional modifications can be made in the amino acid sequence of the hybrid molecules s where those modifications do not significantly impair the ability of the protein to act as a coagulant. For example, the hybrid molecules can also be modified in the activation cleavage site to inhibit the conversion of zymogen Factor VII into its activated two-chain form, as generally described in U.S. Pat. No. 5,288,629, incorporated herein by reference.

The DNA sequences encoding the recombinantly produced part of the hybrid molecules are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the recombinantly produced part of the hybrid molecule is operably linked to additional segments required for transcription of the DNA. In general, the expression vector is derived from plasmid or phage DNA, or may contain elements of both. The term, "operably linked" indicates that the segments are arranged so that they function in concert for their intended purposes, e.g. transcription initiates in a promoter and proceeds through the DNA sequence coding for the polypeptide.

Expression vectors will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

The recombinantly produced parts of the hybrid molecules of the invention are recovered from cell culture medium (either from the medium or by harvesting the bacteria and isolating the polypeptides from there by techniques well-known in the art. Purification mat be attained by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, they may be purified by affinity chromatography on an anti-Factor VII antibody column. The use of calcium-dependent monoclonal antibodies, as described by Wakabayashi et al., J. Biol. Chem. 261:11097-11108, (1986) and Thim et al., Biochemistry 27: 7785-7793, (1988), is particularly preferred. Additional purification may be achieved by conventional chemical purification means, such as high performance liquid chromatography. Other methods of purification, including barium citrate precipitation, are known in the art, and may be applied to the purification (see, for example, Scopes, R., Protein Purification, Springer-Verlag, N.Y., 1982).

For therapeutic purposes it is preferred that the hybrid molecules of the invention are substantially pure. Thus, in a preferred embodiment of the invention the hybrid molecules of the invention are purified to at least about 90 to 95% homogeneity, preferably to at least about 98% homogeneity. Purity may be assessed by e.g. gel electrophoresis and amino-terminal amino acid sequencing.

The Factor hybrid molecule is cleaved at its activation site in order to convert it to its active, two-chain form. Activation may be carried out according to procedures known in the art, such as those disclosed by Osterud, et al., Biochemistry 11:2853-2857 (1972); Thomas, U.S. Pat. No. 4,456,591; Hedner and Kisiel, J. Clin. Invest. 71:1836-1841 (1983); or Kisiel and Fujikawa, Behring Inst. Mitt. 73:29-42 (1983). Alternatively, as described by Bjoern et al. (Research Disclosure, 269 September 1986, pp. 564-565), Factor VII may be activated by passing it through an ion-exchange chromatography column, such as Mono Q® (Pharmacia fine Chemicals) or the like. The resulting activated hybrid molecle may then be formulated and administered as described below.

Assays

The invention also provides suitable assays for selecting preferred hybrid molecules according to the invention. These assays can be performed as a simple preliminary in vitro test.

Thus, Example 1 herein discloses a simple test (entitled "In Vitro Hydrolysis Assay").for the activity of Factor VIIa variants of the invention. Based thereon, Factor VIIa variants which are of particular interest are such variants where the ratio between the activity of the variant and the activity of native Factor VII shown in FIG. 1 is above 1.0, e.g. at least about 1.25, preferably at least about 2.0, such as at least about 3.0 or, even more preferred, at least about 4.0 when tested in the "In Vitro Hydrolysis Assay".

The activity of the variants can also be measured using a physiological substrate such as factor X ("In Vitro Proteolysis Assay") (see Example 2), suitably at a concentration of 100-1000 nM, where the factor Xa generated is measured after the addition of a suitable chromogenic substrate (eg. S-2765). In addition, the activity assay may be run at physiological temperature.

The ability of the Factor VIIa variants to generate thrombin can also be measured in an assay comprising all relevant coagulation factors and inhibitors at physiological concentrations (minus factor VIII when mimicking hemophilia A conditions) and activated platelets (as described on p. 543 in Monroe et al. (1997) Brit. J. Haematol. 99, 542-547 which is hereby incorporated as reference).

Administration and Pharmaceutical Compositions

The hybrid molecules according to the present invention may be used to control bleeding disorders which have several causes such as clotting factor deficiencies (e.g. haemophilia A and B or deficiency of coagulation factors XI or VII) or clotting factor inhibitors, or they may be used to control excessive bleeding occurring in subjects with a normally functioning blood clotting cascade (no clotting factor deficiencies or inhibitors against any of the coagulation factors). The bleedings may be caused by a defective platelet function, thrombocytopenia or von Willebrand's disease. They may also be seen in subjects in whom an increased fibrinolytic activity has been induced by various stimuli.

In subjects who experience extensive tissue damage in association with surgery or vast trauma, the haemostatic mechanism may be overwhelmed by the demand of immediate haemostasis and they may develop bleedings in spite of a normal haemostatic mechanism. Achieving satisfactory haemostasis is also a problem when bleedings occur in organs such as the brain, inner ear region and eyes and may also be a problem in cases of diffuse bleedings (haemorrhagic gastritis and profuse uterine bleeding) when it is difficult to identify the source. The same problem may arise in the process of taking biopsies from various organs (liver, lung, tumour tissue, gastrointestinal tract) as well as in laparoscopic surgery. These situations share the difficulty of providing haemostasis by surgical techniques (sutures, clips, etc.). Acute and profuse bleedings may also occur in subjects on anticoagulant therapy in whom a defective haemostasis has been induced by the therapy given. Such subjects may need surgical interventions in case the anticoagulant effect has to be counteracted rapidly. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

A systemic activation of the coagulation cascade may lead to disseminated intravascular coagulation (DIC). However, such complications have not been seen in subjects treated with high doses of recombinant Factor VIIa because of a localised haemostatic process of the kind induced by the complex formation between Factor VIIa and TF exposed at the site of vessel wall injury. The hybrid molecules according to the present invention may thus also be used in their activated form to control such excessive bleedings associated with a normal haemostatic mechanism.

For treatment in connection with deliberate interventions, the hybrid molecules of the invention will typically be administered within about 24 hours prior to performing the intervention, and for as much as 7 days or more thereafter. Administration as a coagulant can be by a variety of routes as described herein.

The dose of the hybrid molecules ranges from about 0.05 mg to 500 mg/day, preferably from about 1 mg to 200 mg/day, and more preferably from about 10 mg to about 175 mg/day for a 70 kg subject as loading and maintenance doses, depending on the weight of the subject and the severity of the condition.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. The compositions for parenteral administration comprise the Factor VII variant of the invention in combination with, preferably dissolved in, a pharmaceutically acceptable carrier, preferably an aqueous carrier. A variety of aqueous carriers may be used, such as water, buffered water, 0.4% saline, 0.3% glycine and the like. The hybrid molecules of the invention can also be formulated into liposome preparations for delivery or targeting to the sites of injury. Liposome preparations are generally described in, e.g., U.S. Pat. No. 4,837,028, U.S. Pat. No. 4,501,728, and U.S. Pat. No. 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of Factor VII variant in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion can be made up to contain 250 ml of sterile Ringer's solution and 10 mg of the Factor VII variant. Actual methods for preparing parenterally administrable compositions will be known or apparent to those skilled in the art and are described in more detail in, for example, Remington's Pharmaceutical Sciences, 18th ed., Mack Publishing Company, Easton, Pa. (1990).

The compositions containing the hybrid molecules of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject. In general, however, the effective amount will range from about 0.05 mg up to about 500 mg of the Factor VII variant per day for a 70 kg subject, with dosages of from about 1.0 mg to about 200 mg of the Factor VII variant per day being more commonly used.

The FVIIa polypeptides of the present invention may generally be employed in serious disease or injury states, that is, life threatening or potentially life threatening situations. In such cases, in view of the minimisation of extraneous substances and general lack of immunogenicity of human Factor VII polypeptide variants in humans, it may be felt desirable by the treating physician to administer a substantial excess of these compositions comprising the hybrid molecules of the invention.

In prophylactic applications, compositions containing the Factor VII variant of the invention are administered to a subject susceptible to or otherwise at risk of a disease state or injury to enhance the subject's own coagulative capability. Such an amount is defined to be a "prophylactically effective dose." In prophylactic applications, the precise amounts once again depend on the subject's state of health and weight, but the. dose generally ranges from about 0.05 mg to about 500 mg per day for a 70-kilogram subject, more commonly from about 1.0 mg to about 200 mg per day for a 70-kilogram subject.

Single or multiple administrations of the compositions can be carried out with dose levels and patterns being selected by the treating physician. For ambulatory subjects requiring daily maintenance levels, the Hybrid molecules may be administered by continuous infusion using e.g. a portable pump system.

Local delivery of the hybrid molecules of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of hybrid molecule sufficient to effectively treat the subject.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

BRIEF DESCRIPTION OF THE DRAWING

FIG. 1 shows the full amino acid sequence of native (wild type) human coagulation Factor VII (SEQ ID NO: 1).

EXAMPLE 1

In Vitro Hydrolysis Assay

Native (wild-type) Factor VIIa and Factor VIIa variants (both hereafter referred to as "Factor VIIa") are assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

Ratio=$(A_{405\ nm}$ Factor VIIa variant$)/(A_{405\ nm}$ Factor VIIa wild-type).

EXAMPLE 2

In Vitro Proteolysis Assay

Native (wild-type) Factor VIIa and Factor VIIa variants (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

Ratio=$(A_{405\ nm}$ Factor VIIa variant$)/(A_{405\ nm}$ Factor VIIa wild-type).

EXAMPLE 3

Refolding of the Denatured Hybrid Molecules of the Invention

Refolding of incorrectly folded hybrid molecules of the invention is described in Sichler K et al., J. Mol. Biol. (2002) 322, 591-603:

Appropriate folding conditions for denatured FVII is determined by rapid 100-fold dilution of solubilised protein into different folding buffers and incubation for up to 14 days at different temperatures.

The samples are subsequently dialysed against 20 mM Tris (pH 8.5), 5 mM $CaCl_2$, and the soluble fraction is analysed by non-reducing SDS-PAGE.

The optimal folding buffer for denatured native FVII was demonstrated to be 1 M L-arginine, 40% ethylene glycol, 50 mM Tris (pH 8.5), 20 mM CaCl$_2$, 1 mM EDTA. The solubilised protein was added repeatedly into the folding buffer, together with 0.5 mM cysteine, resulting in a concentration of 300 mg/l and incubated at 15° C. for ten days.

It is believed that the same refolding procedure will prove effective with the hybrid molecules of the present invention.

EXAMPLE 4

PEG Conjugation of FVII-(R396C), FVII-(Q250C), FVII-(P406C), FVII-(407C)

The Factor VIIa variants as described in example 1 in WO 02/077218, with a free thiol group introduced at any of the mentioned positions (250, 396, 406 or 407 (the latter C-terminally extended)) are reacted with a 5-fold molar excess of PEG vinylsulfone or PEG-maleimide (alternatively any other sulfhydryl-reactive PEG derivative may be used) in an aqueous buffer for 3 hours to drive the reaction virtually to completion. The molecular weight of the PEG derivative is at least 10,000. The resulting PEG-FVIIa are tested for amidolytic and proteolytic activity as described in examples 1 and 2 and should retain the activity of wild-type human FVIIa, or if a Cys has been introduced into a FVIIa variant with increased activity, the activity after reaction with the PEG derivative should remain higher than that of wild-type human FVIIa. PEG-conjugated FVIIa is separated from unreacted FVIIa variant and free PEG derivative by means of chromatography such as gel filtration on a column of Superdex-200 or the like.

PEG Conjugation of proteins at Cys residues is known to the person skilled in the art and described in several publication including Goodson, R. J. & Katre, N. V. (1990) Bio/Technology 8, 343 and Kogan, T. P. (1992) Synthetic Comm. 22, 2417.

The invention claimed is:

1. A hybrid molecule comprising the amino acid sequence of SEQ ID NO:1 which exhibits the bioactivity of human Factor VII/VIIa, the molecule comprising:
   a) a first polyamino acid that forms a functional lipid membrane binding domain comprising at least one gamma-carboxyglutamic acid residue, and
   (b) a second polyamino acid, which is essentially free of glycoslyation and which is free of gamma-carboxyglutamic residues, said second polyamino acid comprises the amino acid sequence that forms a functional catalytic domain that exhibits human coagulation Factor VII (FVII) or Factor VIIa (FVIIa) activity at least after the hybrid molecule has been subjected to activation by thrombin, Factor IXa, Factor Xa, or Factor XIIa.

2. The hybrid molecule according to claim 1, wherein (i) the first polyamino acid has been prepared by means of chemical peptide synthesis, (ii) the second polyamino acid has been prepared by means of recombinant production in a prokaryotic host cell culture, and (iii) in the first and second parts are joined by a peptide bond or a non-peptide bond, the presence of which does not adversely affect the FVII/FVIIa bioactivity of the hybrid molecule.

3. The hybrid molecule according to claim 1, wherein the first polyamino acid comprises a least 2 γ-carboxyglutamic acid residues.

4. The hybrid molecule according to claim 1, wherein the hybrid molecule is coupled to a bulking agent, said bulking agent is a polyalkylene oxide polymer or a colominic acid.

5. The hybrid molecule according to claim 4, wherein the bulking agent is a polyalkylene oxide polymer or a colominic acid polymer.

6. The hybrid molecule according to claim 1, wherein the first and second polyamino acids comprises at least one non-peptide bond.

7. The hybrid molecule according to claim 1, wherein the first and second polyamino acids are joined by peptide bonds.

8. The hybrid molecule according to claim 7, wherein the presence of non-peptide bond is accompanied by the presence of an oxazolidine, an oxime, a thiazolidine, an acylhydrazone, a triazole, a thioester, or a thioether moiety in the junction region between the first and second polyamino acids.

9. A pharmaceutical composition comprising a hybrid molecule according to claim 1 and a pharmaceutically acceptable carrier or vehicle.

* * * * *

SEQUENCE LISTING

```
<160> NUMBER OF SEQ ID NOS: 1

<210> SEQ ID NO 1
<211> LENGTH: 406
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is gamma-carboxyglutamic acid
<220> FEATURE:
<221> NAME/KEY: MISC_FEATURE
<222> LOCATION: (7)..(7)
<223> OTHER INFORMATION: Xaa is gamma-carboxyglutamic acid
<220> FEATURE:
<221> NAME/KEY: MISC_FEATURE
<222> LOCATION: (14)..(14)
<223> OTHER INFORMATION: Xaa is gamma-carboxyglutamic acid
<220> FEATURE:
<221> NAME/KEY: MISC_FEATURE
<222> LOCATION: (16)..(16)
<223> OTHER INFORMATION: Xaa is gamma-carboxyglutamic acid
<220> FEATURE:
<221> NAME/KEY: MISC_FEATURE
<222> LOCATION: (19)..(19)
<223> OTHER INFORMATION: Xaa is gamma-carboxyglutamic acid
<220> FEATURE:
<221> NAME/KEY: MISC_FEATURE
<222> LOCATION: (20)..(20)
<223> OTHER INFORMATION: Xaa is gamma-carboxyglutamic acid
<220> FEATURE:
<221> NAME/KEY: MISC_FEATURE
<222> LOCATION: (25)..(25)
<223> OTHER INFORMATION: Xaa is gamma-carboxyglutamic acid
<220> FEATURE:
<221> NAME/KEY: MISC_FEATURE
<222> LOCATION: (26)..(26)
<223> OTHER INFORMATION: Xaa is gamma-carboxyglutamic acid
<220> FEATURE:
<221> NAME/KEY: MISC_FEATURE
<222> LOCATION: (29)..(29)
<223> OTHER INFORMATION: Xaa is gamma-carboxyglutamic acid
<220> FEATURE:
<221> NAME/KEY: MISC_FEATURE
<222> LOCATION: (35)..(35)
<223> OTHER INFORMATION: Xaa is gamma-carboxyglutamic acid
<220> FEATURE:
<221> NAME/KEY: DISULFID
<222> LOCATION: (55)..(70)
<220> FEATURE:
<221> NAME/KEY: DISULFID
<222> LOCATION: (72)..(81)
```

```
<220> FEATURE:
<221> NAME/KEY: DISULFID
<222> LOCATION: (91)..(102)
<220> FEATURE:
<221> NAME/KEY: DISULFID
<222> LOCATION: (98)..(112)
<220> FEATURE:
<221> NAME/KEY: DISULFID
<222> LOCATION: (114)..(127)
<220> FEATURE:
<221> NAME/KEY: DISULFID
<222> LOCATION: (135)..(162)
<220> FEATURE:
<221> NAME/KEY: DISULFID
<222> LOCATION: (159)..(164)
<220> FEATURE:
<221> NAME/KEY: DISULFID
<222> LOCATION: (178)..(194)
<220> FEATURE:
<221> NAME/KEY: DISULFID
<222> LOCATION: (310)..(329)
<220> FEATURE:
<221> NAME/KEY: DISULFID
<222> LOCATION: (340)..(368)

<400> SEQUENCE: 1

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
```

-continued

```
                275                 280                 285
Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405
```